United States Patent [19]

Domb

[11] Patent Number: 5,858,296
[45] Date of Patent: Jan. 12, 1999

[54] PREPARATION OF BIOLOGICALLY ACTIVE MOLECULES BY MOLECULAR IMPRINTING

[75] Inventor: Abraham Jacob Domb, Efrat, Israel

[73] Assignee: Yissum Research Development Co. of the Hebrew University of Jerusalem, Jerusalem, Israel

[21] Appl. No.: 857,437

[22] Filed: May 16, 1997

Related U.S. Application Data

[63] Continuation of Ser. No. 476,606, Jun. 7, 1995, Pat. No. 5,630,978.

[51] Int. Cl.[6] ............................................. C08J 5/00
[52] U.S. Cl. ..................... 264/330; 264/108; 264/219; 264/220; 264/221; 264/225; 264/226; 264/227; 264/331.11; 264/331.16; 264/331.19; 264/DIG. 44; 424/78.08; 424/78.37; 526/238.1; 526/238.2
[58] Field of Search ............................. 264/330, 331.11, 264/331.16, 331.19, 108, 219, 220, 221, 225, 226, 227, DIG. 44; 424/78.08, 78.37; 526/238.1, 238.2

[56] References Cited

U.S. PATENT DOCUMENTS 4,334,844  6/1982  Tanaka ........................................ 425/2

*Primary Examiner*—Frederick Krass
*Attorney, Agent, or Firm*—John S. Pratt; Roy D. Meredith; Kilpatrick Stockton

[57] ABSTRACT

A method for preparing mimics of a wide variety of drugs and other biologically active molecules using molecular imprinting techniques, and the mimics produced thereby, is disclosed. Specifically, the mimic is designed by: (i) polymerization of functional monomers around a known drug or biologically active molecule (the template) that exhibits a desired activity; (ii) removal of the template molecule; and then (iii) polymerization of a second class of monomers in the void left by the template, to provide a new organic molecule which exhibits one or more desired properties which are similar to that of the template.

4 Claims, 4 Drawing Sheets

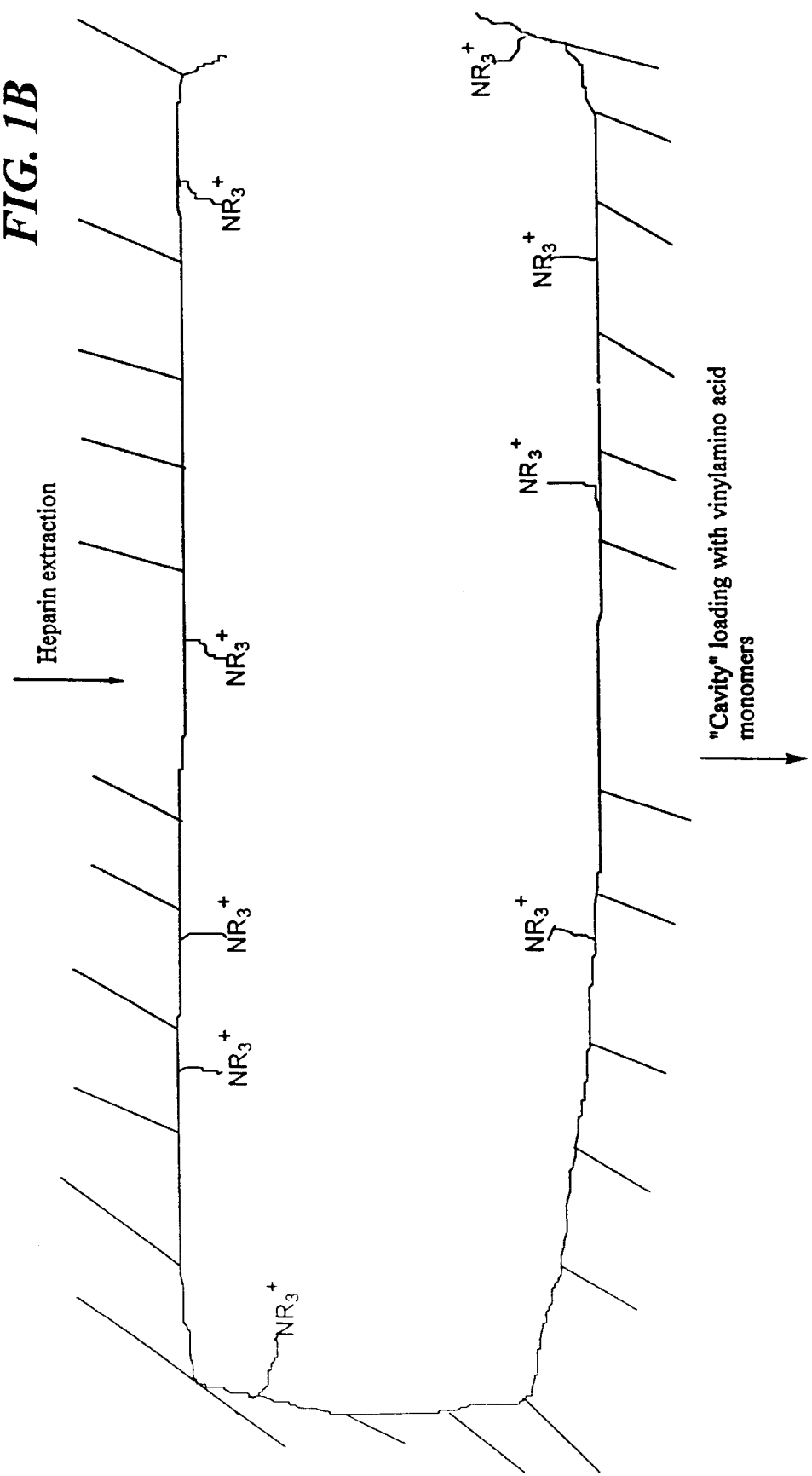

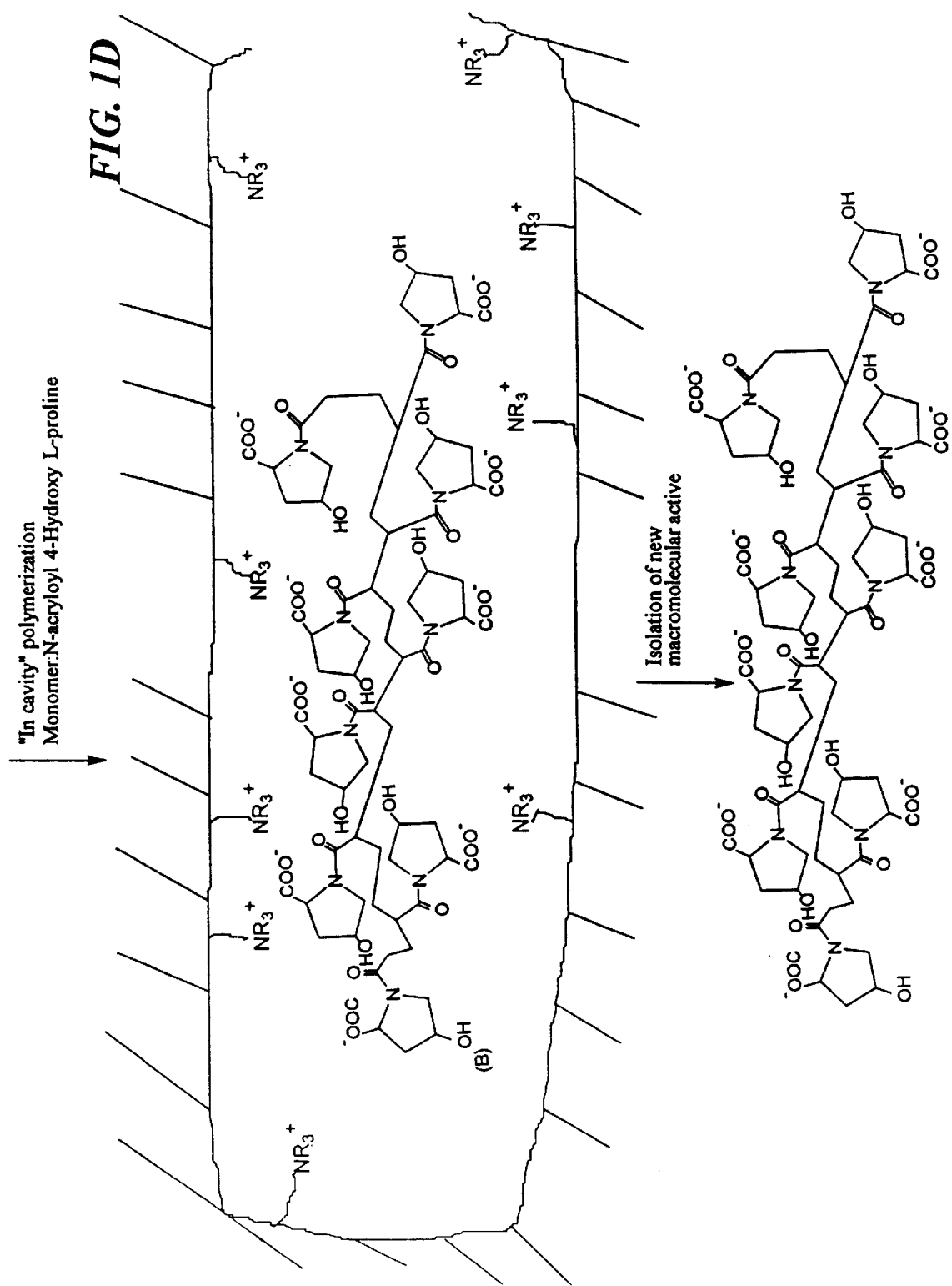

PREPARATION OF BIOLOGICALLY ACTIVE MOLECULES BY MOLECULAR IMPRINTING

This application is a continuation of U.S. Ser. No. 08/476,606, filed Jun. 7, 1995, now U.S. Pat. No. 5,630,978.

This application is in the area of organic synthesis, and in particular discloses to a method for the preparation of organic molecules by molecular imprinting.

The origins of molecular imprinting trace back to the notion of Linus Pauling that the body assembled a new protein complement (i.e., an antibody) by using the foreign intruder as a template!. Although it was later determined that this is not how antibodies are selected in vivo, this template concept stimulated significant thought and research.

In 1972, Wulff and Sarhan demonstrated that a highly crosslinked organic network. polymer could serve as the scaffolding for the molecular imprinting of a template of an organic molecule Wulff, G. and Sarhan, A., *Angew. Chem., Int. Ed., Engl.* 11, 341 (1972). Molecular imprinting now provides an intriguing approach for the de novo construction of macromolecular binding and catalytic sites, as well as sites for the resolution of enantiomers. The polymerization reaction mixture usually consists of a template, polymerizable functional monomers, crosslinking agents, inert solvent, and a free radical initiator. The method involves polymerizing the functional monomers and crosslinking agents in the presence of a "print" or "template" molecule. Prior to polymerization, the monomers spatially distribute themselves about the template in accordance with the size, polarity and functionality of the template. The monomers are then polymerized into a rigid, porous three dimensional network. The template is removed to provide a polymeric network or "macromolecule" which exhibits an imprint of the template. See Kenneth J. Shea, *Molecular Imprinting of Synthetic Network Polymers: The De Novo synthesis of Macromolecular Binding and Catalytic Sites, TRIP* Vol. 2, No. 5, May 1994; Klaus Mosbach, *Molecular Imprinting, Trends in Biochem. Sci.,* 19(9) January 1994; and Wulff, G., in *Polymeric Reagents and Catalysts* (Ford, W. T., Ed.) ACS Symposium Series No. 308, pp 186–230, American Chemical Society (1986).

Two approaches to molecular imprinting have been developed. In the first method, a template is covalently bound to a polymerizable monomer, and after polymerization, the covalent bond is cleaved to release the template from the polymeric mold. In the second method, polymerizable monomers arrange themselves about a template based on noncovalent interactions (such as ionic, hydrophobic, steric, electrostatic, and hydrogen bonding interactions), and after polymerization, the non-covalently bound template is simply leached out.

Molecular imprinting has been used in four areas: (i) chiral stationary phases (CSPs); (ii) antibody mimics; (iii) organic synthesis and enzyme technology as catalytically active polymers or enzyme mimics; and (iv) as sensors in biosensor-like materials, in which the polymers are used as substitutes for the biological molecules normally employed.

Chiral stationary phases prepared by molecular imprinting have achieved impressive separations of racemic mixtures of enantiomers. The polymeric CSP network is prepared using one enantiomer as the template. When a solution of the racemic mixture is then passed through the CSP, the template enantiomer is retained on the column for a significantly longer time than the other enantiomer or enantiomers. In one specific example, macroporous copolymers of ethyleneglycol dimethacrylate (EGDMA) and methacrylic acid (MAA) were prepared in the presence of (—)—S—timolol as the imprinting molecule. Following extraction of the template with acetic acid, the imprinted polymer was able to achieve baseline separation of racemic timolol. The structurally related racemic derivatives atenolol and propranolol were not separated into their enantiomers nor were they retained on the column to any significant degree. Kenneth J. Shea, *Molecular Imprinting of Synthetic Network Polymers: The De Novo synthesis of Macromolecular Binding and Catalytic Sites, TRIP* Vol. 2, No. 5, May 1994. This method has been used to resolve sugars (Wulff, et al., *J. Liq. Chromatography,* 13, 2987–3000 (1990); Wulff, *Macromol Chem.,* 192, 1329–1338 (1991)) amino acid derivatives (Andersson, et al.,*J. Chromatography* 513, 167–179 (1990); Moradian et al, *J. Mol. Recog.,* 2, 167–169 (1989)) and drugs (Fischer, *J. Am. Chem. Soc.* 113, 9358–9360 (1991)).

Molecular imprint polymers have also been prepared that distinguish between nucleoside bases. The molecular basis for the imprinting arises from the fact that adenine and its derivatives are known to form complexes with carboxylic acids. 9-Ethyladenine (9-EA) was thus employed as a template to organize methylmethacrylate monomers prior to copolymerization with N,N'-1,3-phenylene-bis-(2-methyl-2-propenamide) and EGDMA. The 9-EA-imprinted column had a strong affinity for adenine and its derivatives, and the remaining bases eluted close to void volume. Id. Shea, page 168.

Antibody mimics have been prepared using polymeric templates of a compound to evaluate the serum levels of the compound, as a stable alternative to antibodies in conventional immunoassays. For example, anti-theophylline and anti-diazapam MIPs (molecular imprint polymers) have been used to determine theophylline and diazapam concentrations in patient serum samples.

In early research on enzyme mimics, MIPs of transition-state substrate analogs were prepared. In one example, an MIP of p-nitrophenylmethyl phosphonate, a transition state analogue for the hydrolysis of p-nitrophenylacetate was prepared (Lerner, et al., *Science,* 252, 659–667). The MIP exhibited preferential binding of the transition-state analog and induced a small increase in the rate of hydrolysis of p-nitrophenyl acetate to p-nitrophenol. The rate enhancement was specifically inhibited by the transition state analog. Imprints of the enzyme cofactor pyridoxal have been carried out using a stable analog of the Schiff base between pyridoxal and phenylalanine anilide. The MIP was found to modestly enhance the rate of pyridoxal-catalyzed a-proton exchange on $^3$H-labelled phenylalanine anilide.

Several articles have reported using MIPs to direct organic reactions. Wulff, et al., (*Macromol. Chem.* 190, 1727–1735 (1989)) reported the selective reduction of a 3,17-diketosteroid using an MIP that had been prepared with an $LiAlH_2$ group selectively positioned near the keto group that was to be reduced. Muller, et al., (*Macromol. Chem Rapid Commun.* 14, 637–641 (1993)) reported the β-elimination of HF from 4-fluoro-4-(p-nitrophenyl)-2-butanone, using an MIP that had been prepared with a carboxylic acid group selectively positioned opposite the fluorine atom.

Substrate-selective polymers have also been investigated as sensors for those substrates. In one example, a separation process differentiated optical isomers of amino acid derivatives on a column containing molecular imprints made against one enantiomer using streaming potential measurements (Andersson, et al., *J. Chromatography,* 516, 323–331). In another example, optical surface ellipsometry was employed to monitor the specific binding of vitamin K to a surface imprinted silicon surface. Klaus Mosbach, *Molecular Imprinting, Trends in Biochem. Sci.,* 19(9) January 1994.

A number of U.S. patents have issued in the area of molecular imprinting. U.S. Pat. No. 5,110,833 to Mosbach discloses a method for preparing synthetic enzymes and synthetic antibodies using transition state analogues, substrate-like compounds and antigen-like compounds. U.S. Pat. No. 5,321,102 to Loy, et al., discloses molecularly-engineered porous silica materials having micropore in a narrow size range produced through the selective introduction of hydrocarbon templates into the silica structure and their subsequent removal from the solid material structure. U.S. Pat. No. 5,372,719 discloses chemically-produced specific binding "molecular imaged" sorbents which reversibly bind a preselected macromolecule by spatially matched multipoint interactions between functional groups synthesized on the surface of the sorbent and functional groups on the surface of the macromolecule. U.S. Pat. No. 5,310,648 discloses an imprinted matrix that exhibits selective binding interactions through metal chelates with a predetermined molecule or biological particle.

Other U.S. patents that have issuied in this area include: U.S. Pat. No. 5,208,155 entitled "D-Amino Acid Oxidase and Method for Isolation Thereof"; U.S. Pat. Nos. 5,015,576 and 4,935,365 entitled "Macroporous Particles for Cell Cultivation or Chromatography;" U.S. Pat. No. 4,960,762 entitled "Chiral Two-Phase System and Method for Resolution of Racemic Mixtures and Separation of Diastereomers;" U.S. Pat. No. 4,532,232 entitled "Lectin-Containing Separation;" U.S. Pat. No. 4,415,655 entitled "Method of Covalently Binding Biologically Active Organic Substances to Polymeric Substances;" and U.S. Pat. No. 4,406,792 entitled "Separation Agent".

While molecular imprinting has been used for a number of applications, it has not yet been extended to one area of great pharmaceutical interest, namely, preparing mimics of drugs, metabolites and other biologically active molecules, including polysaccharides, peptides and proteins, that retain a desired activity but exhibit improved or different properties. Previous efforts to design such molecules have typically been based on cumbersome structure activity relationships which require the synthesis and evaluation of a number of compounds, molecular modeling, or mere trial and error. It would be of great benefit to have a more simple and direct method to design modified biologically active molecules.

Therefore, it is an object of the present invention to provide a method for the preparation of mimics of drugs and other biologically active molecules that retain a desired activity but exhibit: improved properties.

It is another object of the present invention to provide mimics of drugs, and other biologically active molecules that retain a desired activity but exhibit improved properties.

SUMMARY OF THE INVENTION

A method for preparing mimics of a wide variety of drugs and other biologically active molecules using molecular imprinting techniques, and the mimics produced thereby, is disclosed. Specifically, the mimic is designed by: (i) polymerization of functional monomers around a known drug or biologically active molecule (the template) that exhibits a desired activity; (ii) removal of the template molecule; and then (iii) polymerization of a second class of monomers in the void left by the template, to provide a new organic molecule which exhibits one or more desired properties which are similar to that of the template.

This method provides a unique opportunity to design a wide variety of biological mimics that are more stable than their natural counterparts, because they are typically prepared by the free radical polymerization of functional monomer, resulting in a compound with a nonbiodegradable backbone. This method is thus useful to prepare stable mimics of proteins and peptides, polysaccharides, nucleosides, drugs, nucleoproteins, lipoproteins, carbohydrates, glycoproteins, steroids, lipids, and other biologically active materials.

In one embodiment, biologically active mimics are prepared from polymers with a nonbiodegradable backbone that have pendent amino, amido, carboxylic acid, sulfonic acid, phosphoric acid, or hydroxyl groups, or a combination of these groups. The mimics are prepared by polymerizing or copolymerizing vinyl derivatives that contain these functional groups as the second class of monomers in the process described above. In an alternative embodiment, selected amino acids can be bound to a pre-prepared polymer such as poly(meth)acrylic acid, polysaccharide, or poly(vinyl alcohol).

As an example, using the molecular imprinting method disclosed herein, the polymer N-acryl-trans-hydroxyproline was prepared based on heparin as the template. The polymer was as effective as heparin in inhibiting heparinase, but had less anticoagulating effect.

BRIEF DESCRIPTION OF THE FIGURES

FIGS. 1A–1D is a schematic illustration of one method for the preparation of a heparin mimic using the method disclosed herein.

DETAILED DESCRIPTION OF THE INVENTION

Figure 1A:
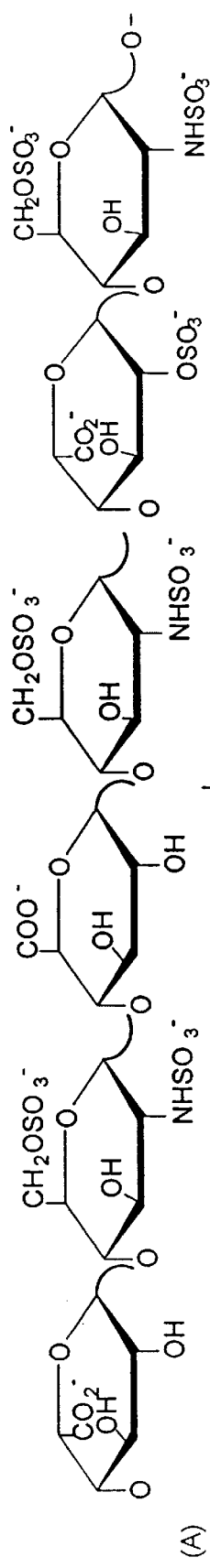
Figure 1A:
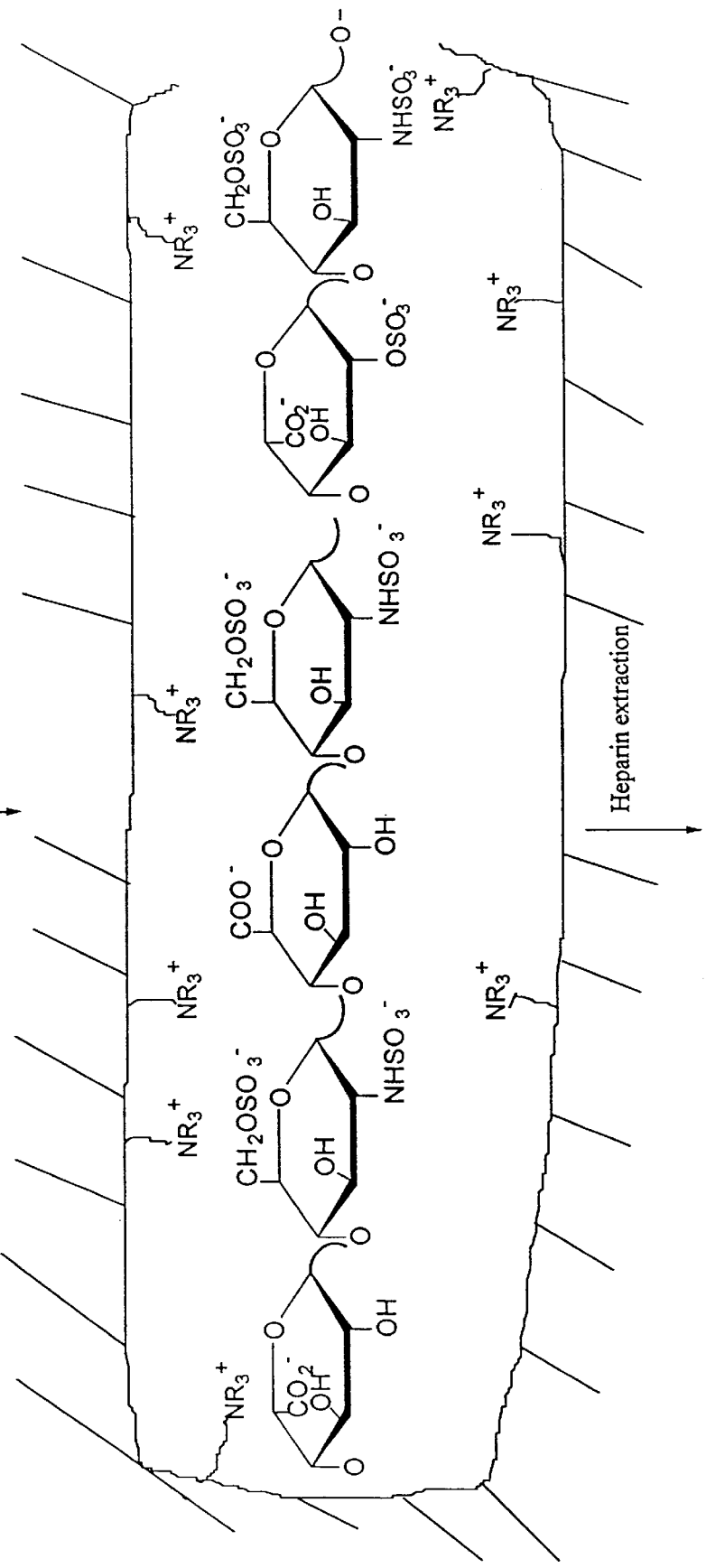
Figure 1C:
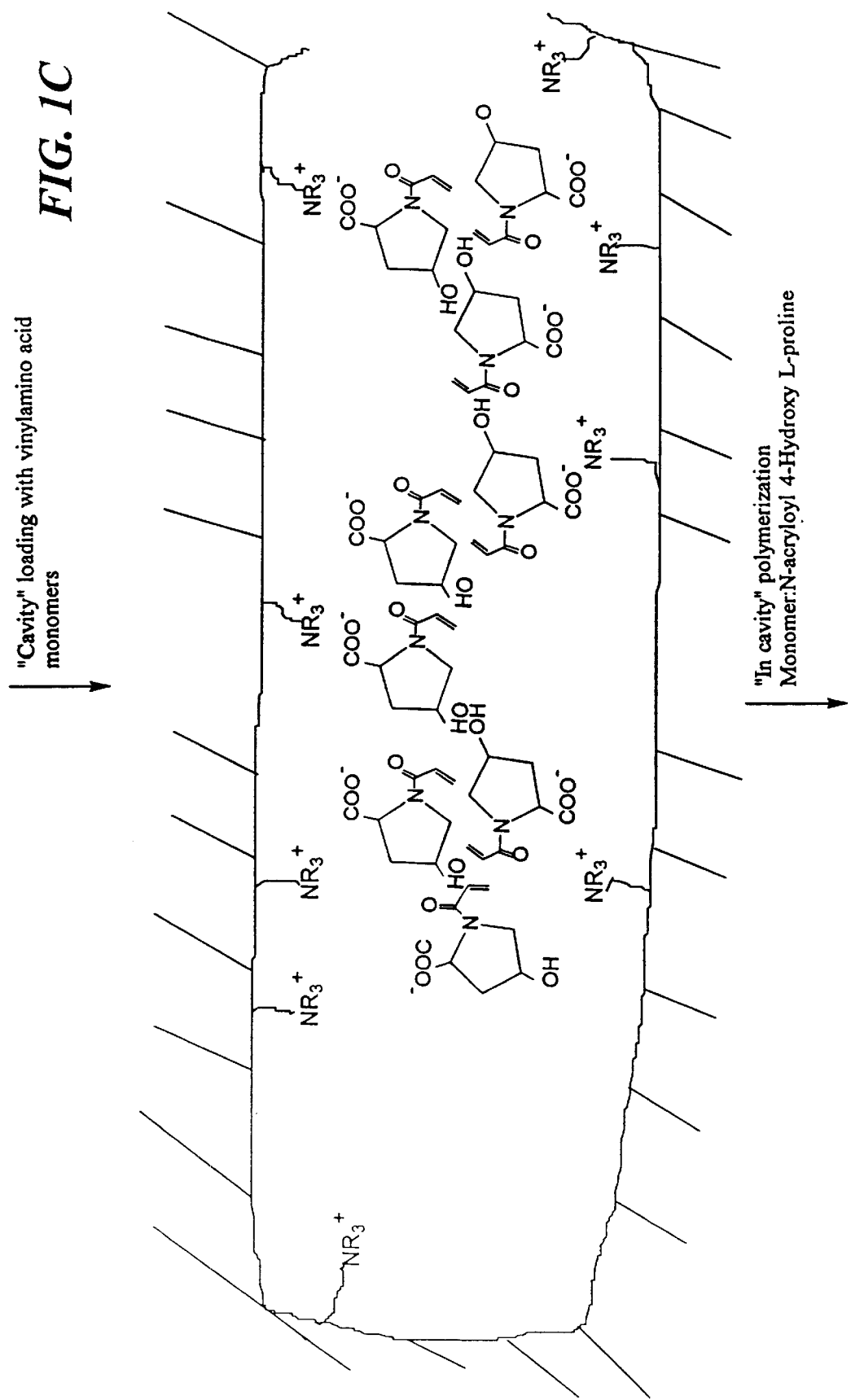

A method for the preparation of mimics of biologically active compounds using molecular imprinting techniques, and the mimics produced thereby, are disclosed. Using this technique, a wide variety of synthetic compounds that exhibit a desired activity of a template molecule can be prepared. A mimic can be designed, for example, that has the biological activity of interest yet is not biodegradable, and therefore, has an increased half life in vivo. Alternatively, a mimic can be designed that is not acted on by an enzyme that would normally convert the template to a more toxic derivative. In yet another embodiment, a mimic is prepared that exhibits one type of activity of the template but not others, allowing the production of boutique compounds with a narrow or simply different spectrum of activity.

As one example, well defined and stable polymeric structures that resemble the outer three dimensional topology of natural biologically active macromolecules, including heparin, peptides such as growth factors, and nucleotides can be prepared. Polymerizable monomers are used for the mimic that contain functional groups that are similar to the outer groups of the naturally occurring biologically active molecule. In one nonlimiting example, vinyl-containing hydroxy amino acids are used. On polymerization, the part of the molecule that contains the amino acid becomes a pendent (i.e., substituent) group off of the hydrocarbon backbone. The free carboxylic acid groups arrange themselves in the molecular imprint polymer prior to polymerization in a manner that, on polymerization, freezes the groups in a biologically active topology.

The term (meth)acrylic refers to methacrylic or acrylic or mixtures thereof.

The term (meth)acrylate refers to methacrylate or acrylate or mixtures thereof.

As used herein, the term acrylate refers to $H_2C=CHCO_2R$, wherein R is an alkyl, aryl, alkaryl or aralkyl group.

The term alkyl, as used herein, unless otherwise specified, refers to a saturated straight, branched, or cyclic, primary, secondary, or tertiary hydrocarbon of $C_1$ to $C_{10}$, and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with any desired moiety, including but not limited to one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term alkaryl or alkylaryl refers to an alkyl group with an aryl substituent.

The term aralkyl or arylalkyl refers to an aryl group with an alkyl substituent.

The term halo, as used herein, includes chloro, bromo, iodo, and fluoro.

The term purine or pyrimidine base includes, but is not limited to, adenine, $N^6$-alkylpurines, $N^6$-acylpurines (wherein acyl is C(O) (alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 6-azapyrimidine, including 6-azacytosine, 2- and/or 4-mercaptopyrimidine, uracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $c^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl.

The term alkenyl, as referred to herein, and unless otherwise specified, refers to a straight, branched, hydrocarbon of $C_2$ to $C_{10}$ with at least one double bond.

As used herein, the term aliphatic refers to an alkyl, alkenyl, or alkynyl group of $C_1$ to $C_{10}$.

I. Selection of Functional Monomers for Production of Molecular Imprint Polymer (MIP)

The polymerization reaction mixture for the preparation of the molecular imprint polymer usually consists of a template, polymerizable functional monomers, which include an effective amount of one or more crosslinking agents to provide a sufficiently rigid structure, inert solvent, and a free radical or other appropriate initiator. Mixtures of monomers and crosslinking agents can be used in the polymerization method.

Two approaches to the production of a molecular imprint polymer have been developed, and either can be used in the method disclosed herein. In the first method, a template is covalently bound to a polymerizable monomer, and after polymerization, the covalent bond is cleaved to release the template from the polymeric mold. Using this method, a selected template is attached to a polymerizable moiety using any appropriate method. The polymerizable template should contain a linkage that can be broken to release the template after the MIP is formed, without adversely affecting the MIP. The bond that is cleaved to release the template can optionally provide an additional polar or ionic site for design and imprinting of the mimic.

In the second method, polymerizable monomers arrange themselves about a template based on noncovalent interactions (such as ionic, hydrophobic, steric, electrostatic, and hydrogen bonding interactions), and after polymerization, the non-covalently bound template is simply Leached out.

Any polymerizable functional initiator, and any monomer, that provides an accurate imprint of the template on polymerization is suitable for use in the present invention. Examples of suitable monomers for use in either of the two approaches discussed above, include, but are not limited to, those described in the references cited in the Background of the Invention. Other suitable monomers can be identified by the skilled artisan given the disclosure herein.

In general, the MIP should exhibit: as closely as possible the reverse topology of the template. For example, if the template has an anionic group at a specific location that is important to the desired biological activity of the mimic, the MIP should have a cationic group at that location. If the template has an cationic group at a specific location that is important to the desired biological activity of the mimic, the MIP should have a anionic group at that location.

Nonlimiting examples of monomers that can be considered in preparing the MIP of a particular template are: methylmethacrylate, other alkyl methacrylates, alkylacrylates, ally or aryl acrylates and methacrylates, cyanoacrylate, styrene, α-methyl styrene, vinyl esters, including vinyl acetate, vinyl chloride, methyl vinyl ketone, vinylidene chloride, acrylamide, methacrylamide, acrylonitrile, methacrylonitrile, 2-acetamido acrylic acid; 2-(acetoxyacetoxy)ethyl methacrylate 1-acetoxy-1,3-butadiene; 2-acetoxy-3-butenenitrile; 4-acetoxystyrene; acrolein; acrolein diethyl acetal; acrolein dimethyl acetal; acrylamide; 2-acrylamidoglycolic acid; 2-acrylamido-2-methyl propane sulfonic acid; acrylic acid; acrylic anhydride; acrylonitrile; acryloyl chloride; (R)-α-acryloxy-β, β'-dimethyl-g-butyrolactone; N-acryloxy succinimide N-acryloxytri.s(hydroxymethyl) aminomethane; N-acryloly chloride; N-acryloyl pyrrolidinone; N-acryloyl-tris (hydroxymethyl)amino methane; 2-amino ethyl methacrylate; N-(3-aminopropyl)methacrylamide; (o, m, or p)-amino-styrene; t-amyl methacrylate; 2-(1-aziridinyl)ethyl methacrylate; 2,2'-azobis-(2-amidinopropane); 2,2'-azobisisobutyronitrile; 4,4'-azobis-(4-cyanovaleric acid); 1,1'-azobis-(cyclohexanecarbonitrile); 2,2'-azobis-(2,4-dimethylvaleronitrile); 4-benzyloxy-3-methoxystyrene; 2-bromoacrylic acid; 4-bromo-1-butene; 3-bromo-3,3-difluoropropane; 6-bromo-1-hexene; 3-bromo-2-methacrylonitrile; 2-(bromomethyl)acrylic acid; 8-bromo-1-octene; 5-bromo-1-pentene; cis-1-bromo-1-propene; β-bromostyrene; p-bromostyrene; bromotrifluoro ethylene; (±)-3-buten-2-ol; 1,3-butadiene; 1,3-butadiene-1,4- dicarboxylic acid 3-butenal diethyl acetal; 1-butene; 3-buten-2-ol; 3-butenyl chloroformate; 2-butylacrolein; N-t-butylacrylamide; butyl acrylate; butyl methacrylate; (o,m,p)-bromostyrene; t-butyl acrylate; (R)-carvone; (S)-carvone; (-)-carvyl acetate; cis 3-chloroacrylic acid; 2-chloroacrylonitrile; 2-chloroethyl vinyl ether; 2-chloromethyl-3-trimethylsilyl-1-propene; 3-chloro--1-butene; 3-chloro-2-chloromethyl-1-propene; 3-chloro-2-methyl propene; 2,2-bis(4-chlorophenyl)-1,1-dichloroethylene; 3-chloro-1-phenyl-1-propene; m-chlorostyrene; o-chlorostyrene; p-chlorostyrene; 1-cyanovinyl acetate; 1-cyclopropyl-1-(trimethylsiloxy) ethylene; 2,3-dichloro-1-propene; 2,6-dichlorostyrene; 1,3-dichloropropene; 2,4-diethyl-2, 6-heptadienal; 1,9-decadiene; 1-decene; 1,2-dibromoethylene; 1,1-dichloro-2, 2-difluoroethylene; 1,1-dichloropropene; 2,6-difluorostyrene; dihydrocarveol; (±)-dihydrocarvone; (-)-dihydrocarvyl acetate; 3,3-dimethylacrylaldehyde; N,N'-dimethylacrylamide; 3,3-dimethylacrylic acid; 3,3-dimethylacryloyl chloride; 2,3-dimethyl-1-butene; 3,3-dimethyl-l-butene; 2-dimethyl aminoethyl methacrylate; 2,4-dimethyl-2,6-heptadien-1-ol; 2,4-dimethyl-2,6-heptadienal; 2,5-dimethyl-1,5-hexadiene; 2,4-dimethyl-1,3-pentadiene; 2,2-dimethyl-4-pentenal; 2,4-dimethylstyrene; 2,5-dimethylstryene; 3,4-dimethylstryene; divinyl benzene; 1,3-divinyltetramethyl disiloxane; 8,13-divinyl-3,7,12,17-tetramethyl-21H,23H-porphine; 8,13-divinyl-3,7,12,17-tetramethyl-21H,23H-propionic acid; 8,13-divinyl-3,7,12, 17-tetramethyl-21H,23H-propionic acid disodium salt; 3,9-divinyl-2,4,8,10-tetraoraspiro[5,5]undecane; divinyl tin dichloride; 1-dodecene; 3,4-epoxy-1-butene; 2-ethyl acrolein; ethyl acrylate; 2-ethyl-1-butene; (±)-2-ethylhexyl acrylate; (±)-2-ethylhexyl methacrylate; 2-ethyl-2-(hydroxymethyl)-1,3-propanediol triacrylate; 2-ethyl-2-(hydroxymethyl)-1,3-propanediol trimethacrylate; ethyl methacrylate; ethyl vinyl ether; ethyl vinyl ketone; ethyl vinyl sulfone; (1-ethylvinyl)tributyl tin; m-fluorostyrene; o-fluorostyrene; p-fluorostyrene; glycol methacrylate (hydroxyethyl methacrylate); GA GMA); 1,6-heptadiene; 1,6-heptadienoic acid; 1,6-heptadien-4-ol; 1-heptene; 1-hexen-3-ol; 1-hexene; hexafluoropropene; 1,6-hexanediol diacrylate; 1-hexadecene; 1,5-hexadien-3,4-diol; 1,4-hexadiene; 1,5-hexadien-3-ol; 1,3,5-hexatriene; 5-hexen-1, 2-diol; 5-hexen-1-ol; hydroxypropyl acrylate; 3-hydroxy-3, 7,11-trimethyl-1,6,10-dodecatriene; isoamyl methacrylate; isobutyl methacrylate; isoprene; 2-isopropenylaniline; isopropenyl chloroformate; 4,4'-isopropylidene dimethacrylate; 3-isopropyl-a-a-dimethylbenzene isocyanate; isopulegol; itaconic acid; itaconalyl chloride; lead (II) acrylate; (±)-:linalool; linalyl acetate; p-mentha-1,8-diene; p-mentha-6,8-dien-2-ol; methyleneamino acetonitrile; methacrolein; [3-(methacryloylamino)-propyl]trimethylammonium chloride; methacrylamide; methacrylic acid; methacrylic anhydride; methacrylonitrile; methacryloyl chloride; 2-(methacryloyloxy)ethyl acetoacetate; (3-methacryloxypropyl)trimethoxy silane; 2-(methacryloxy) ethyl trimethyl ammonium methylsulfate; 2-methoxy propene (isopropenyl methyl ether); methyl-2-(bromomethyl) acrylate; 5-methyl-5-hexen-2-one; methyl methacrylate; N,N'-methylene bisacrylamide; 2-methylene glutaronitrile; 2-methylene-1,3-propanediol; 3-methyl-1,2-butadiene; 2-methyl-1-butene; 3-methyl-1-butene; 3-methyl-1-buten-1-ol; 2-methyl-1-buten-3-yne; 2-methyl-1,5-heptadiene; 2-methyl-1-heptene; 2-methyl-1-hexene; 3-methyl-1,3-pentadiene; 2-methyl-1,4-pentadiene; (±)-3-methyl-1-pentene; (±)-4-methyl-1-pentene; (±)-3-methyl-1-penten-3-ol; 2-methyl-1-pentene; α-methyl styrene; t-a-methylstyrene; t-β-methylstyrene; 3-methylstyrene; methyl vinyl ether; methyl vinyl ketone; methyl-2-vinyloxirane; 4-methylstyrene; methyl vinyl sulfonee; 4-methyl5-vinylthiazole; myrcene; t-β-nitrostyrene; 3-nitrostyrene; 1-nonadecene; 1,8-nonadiene; 1-octadecene; 1,7-octadiene; 7-octene-1,2-diol; 1-octene; 1-octen-3-ol; 1-pentadecene; 1-pentene; 1-penten-3-ol; t-2,4-pentenoic acid; 1,3-pentadiene; 1,4-pentadiene; 1,4-pentadien-3-ol; 4-penten-1-ol; 4-penten-2-ol; 4-phenyl-1-butene; phenyl vinyl sulfide; phenyl vinyl sulfonate; 2-propene-1-sulfonic acid sodium salt; phenyl vinyl sulfoxide; 1-phenyl-1-(trimethylsiloxy) ethylene; propene; safrole; styrene (vinyl benzene); 4-styrene sulfonic acid sodium salt; styrene sulfonyl chloride; 3-sulfopropyl acrylate potassium salt; 3-sulfopropyl methacrylate sodium salt; tetrachloroethylene; tetracyano ethylene; tetramethyldivinyl siloxane; trans 3-chloroacrylic acid; 2-trifluoromethyl propene; 2-(trifluoromethyl) propenoic acid; 2,4,4'-trimethyl-1-pentene; 3,5-bis (trifluoromethyl)styrene; 2,3-bis(trimethylsiloxy)-1,3-butadiene; 1-undecene; vinyl acetate; vinyl acetic acid; 4-vinyl anisole; 9-vinyl anthracene; vinyl behenate; vinyl benzoate; 4-vinyl benzoic acid; vinyl benzyl acetate; vinyl benzyl alcohol; 3-vinyl benzyl chloride; 3-(vinyl benzyl)-2-chloroethyl sulfone; 4-(vinyl benzyl)-2-chloroethyl sulfone; N-(p-vinyl benzyl)-N,N'-dimethyl amine; 4-vinyl biphenyl (4-phenyl styrene); vinyl bromide; 2-vinyl butane; vinyl butyl ether; 9-vinyl carbazole; vinyl carbinol; vinyl cetyl ether; vinyl chloroacetate; vinyl chloroformate; vinyl crotanoate; vinyl cyclohexane; 4-vinyl-1-cyclohexene; 4-vinylcyclohexene dioxide; vinyl cyclopentene; vinyl dimethylchlorosilane; vinyl dimethylethoxysilane; vinyl diphenylphosphine; vinyl 2-ethyl hexanoate; vinyl 2-ethylhexyl ether; vinyl ether ketone; vinyl ethylene; vinyl ethylene iron tricarbonyl; vinyl ferrocene; vinyl formate; vinyl hexadecyl ether; vinylidene fluoride; 1-vinyl imidizole; vinyl iodide; vinyl laurate; vinyl magnesium bromide; vinyl mesitylene; vinyl 2-methoxy ethyl ether; vinyl methyl dichlorosilane; vinyl methyl ether; vinyl methyl ketone; 2-vinyl naphthalene; 5-vinyl-2-norbornene; vinyl pelargonate; vinyl phenyl acetate; vinyl phosphonic acid, bis(2-chloroethyl)ester; vinyl propionate; 4-vinyl pyridine; 2-vinyl pyridine; 1-vinyl-2-pyrrolidinone; 2-vinyl quinoline; 1-vinyl silatrane; vinyl sulfone; vinyl sulfone (divinylsulfone); vinyl sulfonic acid sodium salt; o-vinyl toluene; p-vinyl toluene; vinyl triacetoxysilane; vinyl tributyl tin; vinyl trichloride; vinyl trichlorosilane; vinyl trichlorosilane (trichlorovinylsilane); vinyl triethoxysilane; vinyl triethylsilane; vinyl trifluoroacetate; vinyl trimethoxy silane; vinyl trimethyl nonylether; vinyl trimethyl silane; vinyl triphenyphosphonium bromide (triphenyl vinyl phosphonium bromide); vinyl tris-(2-methoxyethoxy)silane; and vinyl 2-valerate.

Acrylate-terminated or otherwise unsaturated urethanes, carbonates, and epoxies can also be used in the MIP. An example of an unsaturated carbonate is allyl diglycol carbonate (CR-39). Unsaturated epoxies include, but are not limited to, glycidyl acrylate, glycidyl methacrylate, allyl glycidyl ether, and 1,2-epoxy-3-allyl propane.

In an alternative embodiment, silicon-based monomers, as described in U.S. Pat. No. 5,321,102 and elsewhere, can be used in the preparation of the MIP.

Crosslinking agents that lend rigidity to the MIP are known to those skilled in the art, and include di-, tri- and tetrafunctional acrylates or methacrylates, divinylbenzene (DVB), alkylene glycol and polyalkylene glycol diacrylates and methacrylates, including ethylene glycol dimethacrylate (EGDMA) and ethylene glycol diacrylate, vinyl or allyl acrylates or methacrylates, divinylbenzene, diallyldiglycol dicarbonate, diallyl maleate, diallyl fumarate, diallyl itaconate, vinyl esters such as divinyl oxalate, divinyl malonate, diallyl succinate, triallyl isocyanurate, the dimethacrylates or diacrylates of bis-phenol A or ethoxylated bis-phenol A, methylene or polymethylene bisacrylamide or bismethacrylamide, including hexamethylene bisacrylamide or hexamethylene bismethacrylamide, di(alkene) tertiary amines, trimethylol propane triacrylate, pentaerythritol tetraacrylate, divinyl ether, divinyl sulfone, diallyl phthalate, triallyl melamine, 2-isocyanatoethyl methacrylate, 2-isocyanatoethylacrylate, 3-isocyanatopropylacrylate, 1-methy:L-2-isocyanatoethyl methacrylate, 1,1-dimethyl-2-isocyanaotoethyl acrylate, tetraethylene glycol diacrylate, tetraethylene glycol dimethacrylate, triethylene glycol diacrylate, triethylene glycol dimethacrylate, hexanediol dimethacrylate, and hexanediol diacrylate.

Any ratio of simple monomers to crosslinking monomers can be used that provides a structure of appropriate integrity. Those skilled in the art can select suitable ratios of monomers to provide the desired structural integrity.

While free radical polymerization is preferred, monomers can also be selected that are polymerized cationically or anionically. Polymerization conditions should be selected that do not adversely affect the biologically active compound to be mimicked.

II. Selection of Template

Any substrate, including a biologically active compound, and particularly a macromolecule, that exhibits a desired property, can be selected as a template to be imitated synthetically. A macromolecule is a molecule having a molecular weight in the range of two or three thousand to many million. The term biologically active compound or material as used herein refers to an organic molecule including a drug, peptide, protein, carbohydrate (including monosaccharides, oligosaccharides, and polysaccharides), nucleoprotein, mucoprotein, lipoprotein, synthetic polypeptide or protein, or a small molecule linked to a protein, glycoprotein, steroid, nucleic acid (any form of DNA, including cDNA, or RNA, or a fragment thereof), nucleotide, nucleoside, oligonucleotides (including antisense oligonucleotides), gene, lipid, hormone, vitamin, including vitamin C and vitamin E, or combination thereof, that causes a biological effect when administered in vivo to an animal, including but not limited to birds and mammals, including humans. The term drug, as used herein, refers to any substance used internally or externally as a medicine for the treatment, cure, or prevention of a disease or disorder, and includes but is not limited to immunosuppressants, antioxidants, anesthetics, chemotherapeutic agents, steroids (including retinoids), hormones, antibiotics, antivirals, antifungals, antiproliferatives, antihistamines, anticoagulants, antiphotoaging agents, melanotropic peptides, nonsteroidal and steroidal anti-inflammatory compounds, and radiation absorbers, including UV-absorbers. The term biologically active agent also includes agents such as insecticides, pesticides, fungicides, rodenticides, and plant nutrients and growth promoters.

Biological macromolecules are important regulators of physiological functions. The size and tertiary structure of a biologically active macromolecule convey significant chemical information through highly specific interactions with receptors, enzymes, nucleic acids, or other biological mediators interacting with it. Events as diverse as thrombosis, inflammation and immunologic responses are controlled, at least in part, by the three dimensional topology of macromolecules. The surface of the macromolecule is composed of geometrically distributed groups which impart ionic, hydrophobic, steric, electrostatic, and hydrogen bonding character to the molecule and provide the molecular template for receptor binding.

Acid mucopolysaccharides, also referred to as glycosaminoglycans (GAG), consist of recurring disaccharide units, each of which contains a derivative of an aminohexose, usually D-glucosamine or D-galactosamine. At least one of the two sugars in the recurring disaccharide unit of acid mucopolysaccharides contains an acidic group having a negative charge at pH 7, either a carboxylate or a sulfate group. An important acid mucopolysaccharide is heparin, which is generated by certain types of cells that are especially abundant in the lining of arterial blood vessels. Heparin is a very powerful inhibitor of blood clotting and aids in preventing the formation of blood clots in circulating blood. [Jackson, R. L., Busch, S. J., Cardin, A. D., Physiol. Reviews, 71:481–522, 1991].

It is known that GAG is a mediator of cellular processes (humor growth, angiogenesis, nerve cell development, smooth muscle cell proliferation), gene expression and homeostasis. GAG interacts with DNA [Davidson, J. N., in "The biochemistry of the nucleic acids" Methuem, London, 1969].

Both DNA and GAG (for example, heparin) are linear polymers that have polyanionic charges that are essential for biological activity. The rigidity of the DNA helix insures that the specifically sequenced nucleic acids are presented so as to obtain the desired biological interaction. Similarly, the biologically important sequential saccharide units of heparin permit the functional groups to be aligned with the receptor in a highly ordered manner [Chosy J., Lormeu, J. C., Petitou, M., Sinay, P., Freed, J., Ann NY Acad. Sci. 370: 644–649, 1981].

Linear and polyanionic macromolecules such as DNA and GAG, and more generally, carbohydrates, can be used as templates for chemical mimicry using the method disclosed herein. Previous attempts to provide macromolecules that are substitutes for these materials include polyvalent linear macromolecules [Ottenbrite R. M., Polym. Biol. Med. 1, 1–20, 1980); aurintricarboxylic acid (ATA) [Caro, N., Chem. Ber. 25, 939, 1982]; poly (9-vinyladenine) [Noronha-Blob, L., Vengris, V. E., Pitha, P. M., Pitha, J., J. Med. Chem. 20, 356–359, 1977]; poly-(1-vinyluracil) and pyran copolymer (Ottenbrite, R. M. Kuus, K., Kaplan, A. M., J. Macromol. Sci. Chem., A25, 873–893, 1988]; maleic anhydride-styrene copolymers Lewis, F. M., Mayo, F. R., J. Amer. Chem. Soc. 70, 153–1536, 1948); and polyacrylamide sialic acid copolymer [Spaltenstein, A., Whitesides, G. M., J. Amer. Chem. Sci. 113, 686–687, 1991]. These polymers showed a range of biological activities including binding to nucleotides, RNA polymerase, and ribonucleases; inhibition of cytopathic effects of HIV-1, and the prevention of binding of interferon to its receptors and dihydroxyvitamin D3.

Due to the size and polymeric nature of polyanions, different anionic locations on the polymer can have distinct and unique biological activities. Using the method of molecular imprinting, a polyanionic mimic can be prepared that maximizes certain areas of anionic charge and minimizes, or eliminates others, for example, to tailor biological activity as desired.

Proteins are the most abundant macromolecules in cells, making up over half their dry weight. Proteins and peptides are known to carry chemical information in their tertiary structures. A number of proteins occurring in nature are conjugated to other chemical groups. Examples are lipoproteins, glycoproteins, phosphorproteins, hemoproteins, flavoproteins, and metalloproteins.

Proteins have diverse biological functions. Nonlimiting examples are transport proteins (e.g., hemoglobin and serum albumin), nutrient and storage proteins (for example, gliadin, ovalbumin, casein, and ferritin); contractile or motile proteins (e.g., actin, myosin, tubulin, and dynein); structural proteins (for example, keratin, fibroin, collagen, elastin, and proteoglycans); defense proteins (e.g., antibodies, immunoglobulins, fibrinogen, thrombin, botulinus toxin, diphtheria toxin, snake venom, and ricin); enzymes, and regulatory proteins (e.g., insulin, growth hormone, corticotropin and repressors). The molecular imprinting technique described herein can be used to prepare a wide variety of mimics of these important compounds.

Hormones, which are important messengers that convey information based on their chemical structures, can also be used as templates in the method disclosed herein. Hormones are classified as peptide hormones such as thyrotropin-releasing factor, corticotropin, vasopressin, insulin, and glucagon; amine hormones such as adrenaline and thyroxine; or steroid hormones such as cortisol, β-estradiol, testosterone, and progesterone). Other examples of important hormones that can be mimicked include, but are not limited to adrenocorticotropin-releasing hormone, somatotropin releasing hormone, somatostatin, prolactin-releasing hormone, prolactin-inhibitory hormone, FSH- and LH-releasing hormone, vasopressin, and oxytocin.

III. Selection of Second Class of Monomers for Production of Template Mimic

The monomers or mixture of monomers used to prepare the mimic should contain functional or nonfunctional (i.e., steric) groups that are similar to those that impart the desired biological activity to the template. The skilled artisan, given the disclosure herein, will be able to select appropriate monomers among those described herein or otherwise known or available through synthesis. Alkenyl, for example, vinyl, derivatives of amino acids, carbohydrates and nucleosides are particularly useful. Other particularly useful alkenyl monomers are those that contain the same or similar functional group as that in the template, including but not limited to amino, amido, carboxylic acid, sulfonic acid, phosphoric acid and hydroxyl.

If steric interactions are important to the activity of the molecule, monomers should be chosen for polymerization or copolymerization with other monomers that have substituent groups; of approximately the same bulk.

The correct mix of monomers to optimize certain properties, and perhaps minimize other properties, of the template in the mimic can be easily determined once the MIP is prepared.

IV. Preparation of MIP and the Template Mimic

The MIP can be prepared using known methods. In general, the polymerization reaction mixture usually consists of a template, polymerizable functional monomers, crosslinking agents, inert solvent, and a free radical initiator. The template can be covalently bound to a monomer, or can be included in the polymerization mix as a separate species.

The polymerization can be carried out in any solvent that does not adversely affect the reaction. Typical organic solvents are dichloroethane, acetonitrile and methylene chloride.

Any UV or thermal free radical initiator known to those skilled in the art for free radical polymerization can be used to initiate this method. Examples of UV and thermal initiators include benzoyl peroxide, acetyl peroxide, lauryl peroxide, azobisisobutyronitrile, t-butyl peracetate, cumyl peroxide, t-butyl peroxide, t-butyl hydroperoxide, bis(isopropyl)peroxy-dicarbonate, benzoin methyl ether, 2,2'-azobis(2,4-dimethylvaleronitrile), tertiarybutyl peroctoate, phthalic peroxide, diethoxyacetophenone, and tertiarybutyl peroxypivalate, diethoxyacetophenone, 1-hydroxycyclohexyl phenyl ketone, 2,2-dimethyoxy-2-phenyl-acetophenone, and phenothiazine, and diisopropylxanthogen disulfide.

After polymerization, the template is removed in a manner that does not adversely affect the imprint. If the template is covalently bound, it is removed using the mildest conditions possible for the cleavage of the covalent bond.

V. Examples of a Method for the Preparation of the Template Mimic

Given the disclosure herein, one of skill in the art will be able to prepare a wide variety of mimics of substances of interest. The examples below describe nonlimiting methods for preparing mimics of heparin and serum albumin. These examples are not intended to limit the scope of the invention, which is a method for the production of mimics generally.

Heparin is a molecule with a unique topology. It has multiple biological activities which are experimentally easy to determine, and therefore is a good model compound for this method. It would be useful to provide a heparin mimic that exhibits one or more activities of heparin and not others. To accomplish this result, macromolecular heparin-like structures with heparin topology were synthesized.

In the first step, a polymer imprint of heparin active site was prepared by polymerizing a mixture of divinyl acrylic monomers and vinyl monomers with amino side chains in the presence of various amounts of heparin. After polymerization, the embedded heparin was leached-out leaving a heparin print, with an inverse topology to heparin. The printed acrylic polymer was loaded with a mixture of N-acryl hydroxyproline and acrylic monomers. The amino acid monomers were arranged within the printed cavity by acid-base salt formation with the functional groups representing the inverse topology of heparin. The loaded vinyl monomers in the cavities were then polymerized to yield a "heparin" topology. The biological activity of the reprinted molecule was then evaluated and compared with that of heparin.

Materials and Methods

All solvents were of analytical grade and purchased from Frutarom. 4-Hydroxyproline was purchased from Aldrich.

NMR spectra were recorded on a Varian-VXR 300 spectrometer. The shifts are expressed in ppm. Melting points were measured at an Electrothermal 9200 apparatus. Elemental Analyses were done at The Elemental Analysis Laboratory of The Hebrew University. TLC analysis: Silica gel 60 plates with indicator F254 of 0.2 mm thick were used and run with 5% MeOH in dichloromethane. Liquid chromatography was performed using Silica gel 60 mesh 70–230 to package columns of 2.5–30 cm.

EXAMPLE 1

4-Hydroxyproline hydrochloride methyl ester

4-Hydroxyproline (2.00 grams; 15.2 mmol) were mixed with 100 ml of methanol. Dry HCl was bubbled into the mixture for 20 minutes. All of the solid dissolved in a few minutes. The solution was stirred for 10 additional minutes and concentrated to about 30 ml. Ether was added until precipitation started. After cooling, the precipitate was filtered and washed with ether to yield 2.57 grams (93%) of 4-hydroxyproline hydrochloride methyl ester. M.P. 176° C. $^1$H-NMR (D20): 4.70 (2 H, m); 3.85 (3 H, m); 3.45 (2 H, dq); 2.50 (1 H, m); 2.30 (1 H, m).

EXAMPLE 2

Preparation of N-Acroyl Amino Acid Polymer

Scheme 1:
General scheme of polymer preparation.

General scheme of polymer preparation.

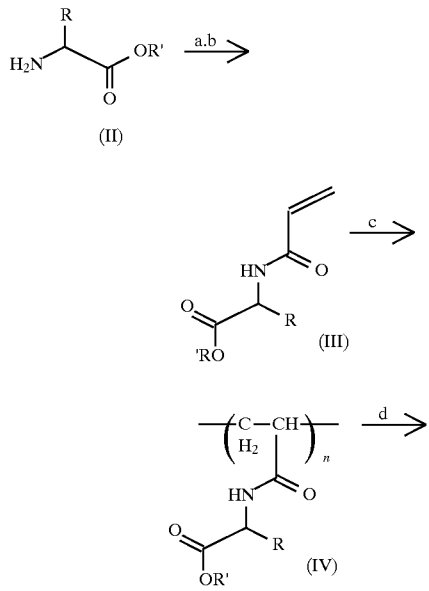

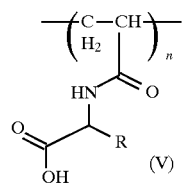

Reagents: a) acryloyl chloride; b) triethyl amine; c) Radical polymerization by

General Procedures

N-Acryloyl Aminoacids Esters (III).

A protected aminoacid (II) (12.5 mmol) (prepared according to standard procedures) was dissolved in dichloromethane (100 mL) containing triethylamine (3.40 ml, 2.1 eq.). The solution was cooled to 0° C. and a solution of acryloyl chloride (1.04 mL, 1.1 eq.) in dichloromethane (10 mL) was slowly dropped (over one hour). The cooling bath was removed and the mixture stirred overnight. The solution was diluted and washed twice with 1M $NaHSO_4$ (about 5 ml). The organic layer was dried over $MgSO_4$, liltered and concentrate by flash evaporation. Some of the products crystalize (MeOH/ether or ether/hexane). The aminoacids containing side chain functions (hydroxyprolines and tyrosine) were purified by silica-gel column chromatography with a gradient of 0 to 5% MeOH in dichloromethane as eluent.

Results and physical data are shown below in Table 1. In most cases, satisfactory elemental analysis was obtained. For aminoacids 4-cis-hydroxy-D-proline and L-proline the N-acryloyl derivative wasn't stable and polymerize readily on purification.

TABLE 1

Structure and physical data of synthesized monomers.

| MONOMER | M.P. (°C.) | H-NMR ($CDCl_2$, δ = ppm) | ELEMENTAL ANALYSIS |
|---|---|---|---|
| HO,,,⟨pyrrolidine with N-acryloyl, CO2Me⟩ | 77–78 | 6.40(2H, m), 5.74(1H, m), 4.67(2H, m)3.87(1H, dd), 3.75(3H, s), 3.61(1H, m), 2.73(1H, broad), 2.30(1H, m), 2.10(1H, m) | Calc: C: 54.26; H: 6.58 Found: C: 54.54; H: 6.78 |
| HO,⟨pyrrolidine with N-acryloyl, CO2Me⟩ | Syrup | 6.42(2H, d), 5.76(1H, t), 4.60(1H, d)4.45(1H, m), 3.80(5H, s), 2.35(1H, m), 2.12(1H, m), 1.63(1H, broad) | — |
| ⟨acryloyl-HN-CH(CH2Ph)-CO2Me⟩ | 81–83 | 7.27–7.09(5H, m), 6.30(1H, d), 6.12(1H, m), 6.05(1H, broad), 5.65(1H, d), 4.97(1H, q), 3.74(3H, s), 3.17(2H, t). | Calc: C: 66.91; H: 6.18 Found: C: 67.20; H: 6.39: |

TABLE 1-continued

Structure and physical data of synthesized monomers.

| MONOMER | M.P. (°C.) | H-NMR (CDCl$_2$, δ = ppm) | ELEMENTAL ANALYSIS |
|---|---|---|---|
| (structure: N-acryloyl pyrrolidine-2-CO$_2$Bu$^t$) | Syrup | 6.40(2H, m), 5.67(1H, dd), 4.40(1H, m)3.68(2H, m), 2.14(2H, m), 1.96(2H, m)1.44(9H, s). | — |
| (structure: HO-phenyl-CH$_2$-CH(CO$_2$Bu$^t$)-NH-acryloyl) | 108 | 6.97(2H, d), 6.73(2H, d), 6.60(1H, hmad), 6.25(1H, d), 6.19(1H, d), 6.09(1H, m), 5.65(1H, d), 4.80(1H, q), 3.03(2H, m), 1.43(9H, s). | Calc: C: 65.95; H: 7.27 Found C: 66.65; H: 7.50; |
| (structure: acryloyl-NH-CH$_2$-CO$_2$Bu$^t$) | 55–56 | 6.32(1H, d), 6.16(1H, m), 6.10(1H, broad) 5.67(1H, d), 4.02(2H, d), 1.47(9H, s). | Calc: C: 58.36; H: 8.16 Found: C: 58.42; H: 8.21; |
| (structure: acryloyl-NH-CH(C(CH$_3$)$_3$)-CO$_2$Bu$^t$) | 115 | 6.31(1H, d), 6.16(1H, m), 6.11(1H, broad), 5.67(1H, d), 4.45(1H, d), 1.46(9H, s), 1.00(9H, s). | Calc: C: 64.70; H: 9.61 Found: C: 64.69; H: 9.81; |

Polymerization of N-Acryloyl Aminoacids Esters (IV).

Polymerizations were carried out in bulk polymerization by adding 0.5% (W/W) benzoyl peroxide to the monomer and heating to 70° C. for five hours or in solvent. The solvent was either toluene, using the above-mentioned initiation, or water-methanol, using ammonium persulfate as initiator. After polymerization, the solvent was evaporated and the polymer precipitated usually adding ether and hexane to the crude.

Deprotection of the Resulting Polymer (V).

Methyl esters were hydrolyzed with LiOH (about 2 equivalents) in 1:1 acetonitrile:water. The acetonitrile was evaporated, the water solution acidified and lyophilized. The polymer was precipitated by adding either to the methanolic solutions.

Tert-butyl esters were hydrolyzed by a mixture of 50% trifluoroacetic acid in dichloromethane. The solution was concentrated and the polymers precipitated by adding either ether or petroleum ether.

Results and physical data of the polymers are shown in Table 2. In Table 2, a+ indicated complete inhibition, −+ indicates inhibition, but not complete, and−indicates no effect.

TABLE 2

Polymer structure and heparinase inhibition activity: (a: 1:1 MeOH/H$_2$O; b: MeOH; c: 2.5% Na$_2$CO$_3$ in 1:1 MeOH/H$_2$O.

| Substance | Symbol | η$^{25}$ (solvent) | Activity at 1 μg/ml | at 10 μg/ml |
|---|---|---|---|---|
| (polymer structure with COOLi, pyrrolidine, OH) | AB-34 | 1.76(a) | − | + |
| (polymer structure with COOLi, pyrrolidine, OH) | AB-41 | 0.10(b) | − | − |

TABLE 2-continued

Polymer structure and heparinase inhibition activity: (a: 1:1 MeOH/H$_2$O; b: MeOH; c: 2.5% Na$_2$CO$_3$ in 1:1 MeOH/H$_2$O.

| Substance | Symbol | $\eta^{25}$ (solvent) | Activity at 1 µg/ml | at 10 µg/ml |
|---|---|---|---|---|
| [structure] | AB-78 | 0.06(b) | − | −+ |
| [structure] | AD-79 | 0.19(b) | − | + |
| [structure] | AB-85(B) | 0.12(c) | − | + |
| [structure] | AB-86 | 0.44(c) | −+ | + |
| [structure] | AB-88 | 1.11(c) | −+ | + |
| [structure] | AB-89 | 0.22(c) | − | + |
| [structure] | AB-90(II) | 0.30(b) | − | − |

+ complete inhibition
−+ inhibition but not complete
− no effect

EXAMPLE 3

N-Acryloyl-4-Hydroxyproline methyl ester

4-Hydroxyproline hydrochloride methyl ester (2.11 grams; 12.5 mmol) were dissolved in 100 ml of dichloromethane containing 3.40 ml (2.1 eq.) of triethylamine. The solution was cooled to 0° C. and a solution of 1.04 ml of acryloyl chloride (1.1 eq.) in 10 ml of dichloromethane was slowly added. The cooling bath was removed and the mixture stirred overnight. The solution was diluted and washed with 1M NaHS04 (about 5 ml). The organic layer was dried over MgSO4, filtered and concentrated by flash evaporation to yield an oily residue. The crude product was purified by silica gel liquid chromatography (1 to 5% methanol in dichloromethane). The fractions containing the spot at Rf=0.2 were combined. The solvent was removed and the oily residue crystallized from ethyl acetate to yield 1.28 grams (52%) of N-acryloyl-4-hydroxyproline methyl ester. M.P. 77°–78° C. $^1$H NMR (CDC13); 6.40 (1 H, m); 5.70 (1 H, m); 4.60 (2 H, m); 3.85 (1 H, m); 3.75 (3 H, s); 2.65 (1 H, broad); 2.30 (1 H, m); 2.10 (1 H, m); 1.70 (1 H, s). Elemental analysis ($C_9H_{13}NO_4$): calculated C=54.26%, H=6.58%, N=7.03%. Found C=54.54%, H=6.78%, N=7.24%.

N-acryl derivatives of cis-4-hydroxyproline, tyrosine, phenylalanine, tryptophane, and other amino acids were prepared similarly.

EXAMPLE 4

Poly(N-Acryloyl-4-hydroxyproline methyl ester)

Polymers based on N-Acryloyl-4-Hydroxyproline were synthesized using the molecular casting method or by radical polymerization in solution.

In the solution polymerization technique, 200 mg of N-acryloyl-4-hydroxyproline methyl ester were dissolved in dry toluene (10 ml). The solution was degassed and 1 mg of benzoyl peroxide was added. The mixture was heated to 80° C. for 3 hours. The toluene was removed and the white residue was triturated with ether, filtered and dried. Copolymers with acrylic acid, methacrylic acid, aminoethyl methacrylate, and various-acryl amino acids were prepared similarly. N-Propenyl derivatives of amino acids were polymerized and copolymerized using the same method.

EXAMPLE 5

De-methylation of the resulting polymer

Poly(N-acryloyl-4-hydroxyproline methyl ester) was dissolved in a 1:1 0.5M LiOH:acetonitrile mixture (1 eq. of LiOH), and the solution was stirred overnight. The acetonitrile was removed by flash evaporation and the water was removed by lyophilization. Density=1.76 g/cc (solution of 1% polymer in 1:1/MeOH:$H_2O$).

EXAMPLE 6

Preparation of N-propenyl-4-trans-hydroxyproline

Propenyl bromide (1.1 eq) was added dropwise (over one hour) to a solution of 4-hydroxyproline hydrochloride methyl ester (1 equiv.) in toluene containing 2.1 eq. of triethylamine. The reaction mixture was heated to 60° C. and stirred overnight. The solution was washed with 1M $NaHSO_4$. The organic layer was dried over $MgSO_4$, filtered and concentrated by flash evaporation to an oily residue. The crude product was purified by silica-gel liquid chromatography (1 to 5% methanol in clichloromethane). The solvent was removed and the oily residue crystallized in ethyl acetate.

N-propenyl derivatives of cis-4-hydroxyproline, tyrosine, phenylalanine, tryptophane, and other amino acids are prepared similarly.

EXAMPLE 7

Molecular Imprint of Heparin

The imprinting of low molecular weight heparin (MW= 4,000) was performed as follows: ethyleneglycol dimethacrylate, methacrylic acid, aminoethyl-methacrylate and hydroxyethylmethacrylate in a ratio of 70:10:5:15 v/v were mixed. A concentrated solution of heparin in water (100 mg in 100 µl of water) was added to 2 ml of the monomer mixture, along with a redox catalyst, 5µl of 10% w/v $Na_2S_2O_5$, 5 µl of 10% w/v $Na_2S_2O_8$, and 5 µl of 1% $Fe(NH_4)_2(SO_4)_2$ were added and mixed well. The mixture was left to polymerize at 25° C. for 24 hours to yield a solid block. The polymer was ground to a powder and immersed at room temperature in deionized water over night. The powder was isolated by filtration and lyophilized to dryness to yield imprinted polymer containing specific cavities for heparin.

Molecular casting was performed by mixing the dry powder (1 gram) in an acetone-water solution (2 ml) containing 100 mg of N-acryl trans-L-hydroxyproline, methacrylic acid and aminoethylmethacrylate in a ratio 10:1:1 w/w and a redox catalyst, 5 µl of 0.01% w/v $Na_2S_2O_5$, 5 µl of 0.01% w/v $Na_2S_2O_8$, and 5 µl of 0.001% $Fe(NH_4)_2(SO_4)_2$. The acetone was evaporated under vacuum at room temperature and left to polymerize over night. The product was extracted using acidic water solution and lyophilized to yield short polymers which show biological activity like heparin.

EXAMPLE 8

Imprinting of Heparin using anhydrous medium

Heparin was imprinted according to the procedure taught by Mosbach [Sellergren, B., Lepisto, M., and Mosbach, K., J. Am. Chem. Soc., 110, 5853–5860, 1988], the contents of which are hereby incorporated by reference. Heparin sodium (Sigma, 1.5 mmol per saccharide units), methacrylic acid (5 mmol), hydroxyethyl methacrylate (2 mmol), ethylene glycol dimethacrylate (30 mmol) and azobisisobutyronitrile (AIBN) (0.4 mmol) were mixed in 5 ml of either acetonitrile, DMF, methanol, or ethylacetate. The mixture was degassed with a nitrogen stream, sealed in borosilicate glass ampules, and thermally polymerized at 45° C. overnight. Alternatively, the ampules were placed in a 0° C. ice bath and irradiated at 366 nm UV light for 10 hours. The resulting polymer was ground to powder and immersed in acetonitrile: acetic acid: water 9:1:1 overnight. The powder was dried and used for molecular casting as described in the previous example.

EXAMPLE 9

Determining the biological activity of the polymers

The biological activity of the polymers was determined by: 1) inactivation of heparanase enzyme; 2) release of extracellular matrix (ECM) bound FGF, and 3) blood clotting using APTT standard method. In addition, the polymers based on cis-hydroxyproline were tested for antifibrotic activity. Poly(N-acryl 5-hydroxyproline) was as active as heparin in deactivating heparinase in a concentration of less than 1 mg/mL.

The free acid polymer released only 15–20% of extracellular matrix (ECM) bound FGF as compared to 80% for heparin, and had only 20% anticoagulation activity compared to heparin. These results suggest that the new polymer is more selective than heparin, which implies that the polymer may act as a smooth muscle proliferation inhibitor without the side-effects of anticoagulation. This is apparently the first compound to show high activity as heparanase inhibitor with little activity as anticoagulant and FGF release agent.

Similar compounds were synthesized and tested for their biological activity.

EXAMPLE 10

Release of extracellular matrix (ECM) bound FGF

The polymers were tested according to the method of Vlodavsky [Vlodavsky, I., Bar-Shavit, R., Korner, G., and Foks, Z., Extracellular matrix-bound growth factors, enzymes, and plasma proteins, in Molecular and cellular aspects of basement membrane, Academic Press, 327–343 (1993)]. Release of ECM bound bFGF was low (15%) at the concentration range between 1 and 25 mg/ml for N-acryl-4-hydroxyproline based polymers. Under the same conditions, heparin released about 80% of the ECM bound bFGF at a concentration of 2 to 25 mg/ml. The methyl ester derivative of this polymer was completely inactive.

EXAMPLE 11

Anticoagulation activity (APTT)

The anticoagulation activity was determined as follows: 100 μl of normal pooled plasma (George King Biomedical Inc., Kansas) and 100 ml of a solution containing the test compound in aqueous 50 mM Tris hydrochloride at pH 7.5 (0.2 mg of sample in 1.0 ml buffer) were added to an assay cuvette. The sample was placed in a MLA coagulation timer, which automatically maintained the sample of 37° C. for 2.5 minutes, and 100 μl of actin activated cephaloplastin reagent was injected. After 5 minutes 100 μl of 35 mM $CaCl_2$ was injected and clot formation was determined photometrically and the clotting time was recorded. Each sample was examined at a variety of concentrations, generally from 0.025 mg/ml to about 1 mg/ml, and the clotting times were graphed as a function of concentration. From the graphic results, the concentration required to double clotting time (ICDCT) was calculated by linear interpolation.

Poly(N-acryl-trans-5-hydroxyproline) prepared by solution polymerization was compared to heparin using this test and found to exhibit 20% of the activity of heparin. The polymers based on N-acryl trans-5-hydroxyproline prepared by the molecular casting method were less active than heparin in blood coagulation but more effective than the solution polymerized poly(N-acryl trans-5-hydroxyproline). The methyl ester derivative of the polymer did not show any anticoagulant activity even at high concentrations.

EXAMPLE 12

Antifibrotic activity

Cis-hydroxy-L-proline is an inhibitor of the biosynthesis of collagen and is used as an antifibrotic agent for treating lung fibrosis [Poiani, G. J., Tozzi, C. A., Choe, J. K., Yohn, S. E., and Riley, D. J., J. Appl. Physiol. 68(4), 1542, 1990.]. Poly(acryl-cis-hydroxy-L-proline) was; tested for its antifibrotic activity using an in vitro assay [Kao, W. W. and Prokop, D. J., Nature, 63, 1977] where the polymer is added to cultures of smooth muscle cells and fibroblasts seeded on plastic dishes in a medium containing 10% fetal bovine serum. The MIC (minimum inhibitory concentration) was significantly lower than that of cis-hydroxy-L-proline and the activity of the polymer was prolonged for one week.

EXAMPLE 13

Casting of bovine serum albumin (BSA)

The imprinting method of BSA was performed as above using a mixture of N-acryl trans-L-hydroxyproline, methacrylic acid ethyleneglycol dimethacrylate and styrene at a ratio 5:2:0.01:1 w/w. A cast molecule that mimics BSA was obtained.

Modifications and variations of the present invention will be obvious to those skilled in the art from the foregoing detailed description of the invention. Such modifications and variations are intended to come within the scope of the appended claims.

We claim:

1. A biologically active compound prepared by the method of (a) polymerization of functional monomers around a template molecule that exhibits a biological activity;

(b) removal of the template molecule; and (c) polymerization of a second class of monomers in the void left by the template to give a biologically active compound.

2. The compound of claim 1, wherein the template is a macromolecule.

3. The compound of claim 2, wherein the macromolecule has an absolute molecular weight of two thousand to three million.

4. The compound of claim 3, wherein the template molecule is selected from the group consisting of carbohydrates, oligosaccharides, polysaccharides, steroids, nucleic acids, nucleotides, nucleosides, oligonucleotides, genes, and vitamins.

* * * * *